United States Patent
Al-Ali

(10) Patent No.: US 11,488,715 B2
(45) Date of Patent: Nov. 1, 2022

(54) MEDICAL CHARACTERIZATION SYSTEM

(71) Applicant: Masimo Corporation, Irvine, CA (US)

(72) Inventor: Ammar Al-Ali, San Juan Capistrano, CA (US)

(73) Assignee: Masimo Corporation, Irvine, CA (US)

(*) Notice: Subject to any disclaimer, the term of this patent is extended or adjusted under 35 U.S.C. 154(b) by 161 days.

(21) Appl. No.: 16/445,050

(22) Filed: Jun. 18, 2019

(65) Prior Publication Data

US 2019/0304605 A1    Oct. 3, 2019

Related U.S. Application Data

(63) Continuation of application No. 13/371,767, filed on Feb. 13, 2012, now Pat. No. 10,332,630.

(Continued)

(51) Int. Cl.
*G16H 50/20* (2018.01)
*A61B 5/0205* (2006.01)
(Continued)

(52) U.S. Cl.
CPC ......... *G16H 50/20* (2018.01); *A61B 5/02055* (2013.01); *A61B 5/7275* (2013.01);
(Continued)

(58) Field of Classification Search
CPC ... A61B 5/02055; A61B 5/7275; A61B 5/333; A61B 5/022; A61B 5/087; A61B 5/14551; G16H 50/20; G16H 50/30
See application file for complete search history.

(56) References Cited

U.S. PATENT DOCUMENTS 4,960,128 A  10/1990  Gordon et al.
4,964,408 A  10/1990  Hink et al.
(Continued)

FOREIGN PATENT DOCUMENTS

JP   2009-066269    4/2009
WO   WO 03/091838   11/2003
(Continued)

OTHER PUBLICATIONS

Apiletti et al., "SAPhyRA: Stream Analysis for Physiological Risk Assessment", Twentieth IEEE International Symposium on Computer-Based Medical Systems (CBMS '07), 2007, pp. 6.
(Continued)

*Primary Examiner* — Mallika D Fairchild
*Assistant Examiner* — Shreya Anjaria
(74) *Attorney, Agent, or Firm* — Knobbe Martens Olson & Bear, LLP

(57) ABSTRACT

A medical characterization system is configured to input medical-related continuous parameters and discrete data so as to calculate a characterization timeline indicative of a physiological condition of a living being. A data source is in sensor communications with a patient so as to generate a continuous parameter. The data source also provides test data responsive to the patient at a test time. The test data is available to a characterization processor at a result time. The characterization processor is also responsive to the continuous parameter so as to generate a medical characterization as a function of time. A characterization analyzer enables the characterization processor to update the medical characterization in view of the test data as of the test time.

16 Claims, 15 Drawing Sheets

Related U.S. Application Data

(60) Provisional application No. 61/442,264, filed on Feb. 13, 2011.

(51) Int. Cl.
*A61B 5/00* (2006.01)
*A61B 5/022* (2006.01)
*A61B 5/087* (2006.01)
*A61B 5/1455* (2006.01)
*G16H 50/30* (2018.01)
*A61B 5/333* (2021.01)

(52) U.S. Cl.
CPC .............. *A61B 5/022* (2013.01); *A61B 5/087* (2013.01); *A61B 5/14551* (2013.01); *A61B 5/333* (2021.01); *G16H 50/30* (2018.01)

(56) References Cited

U.S. PATENT DOCUMENTS

| | | | |
|---|---|---|---|
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| 5,355,889 | A * | 10/1994 | Nevo .................. A61B 5/0205 600/484 |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,685,299 | A | 11/1997 | Diab et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,066,204 | A | 5/2000 | Haven |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,115,673 | A | 9/2000 | Malin et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,223,064 | B1 * | 4/2001 | Lynn .................. A61B 5/14551 600/324 |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |

(56) References Cited

U.S. PATENT DOCUMENTS

| | | |
|---|---|---|
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |

(56) References Cited

U.S. PATENT DOCUMENTS

| | | | |
|---|---|---|---|
| 7,647,083 B2 | 1/2010 | Al-Ali et al. |
| 7,647,185 B2 | 1/2010 | Tarassenko et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,801,591 B1 | 9/2010 | Shusterman |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,275,553 B2 * | 9/2012 | Ochs ............... A61B 5/316 702/19 |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |

(56) References Cited

U.S. PATENT DOCUMENTS

| | | | |
|---|---|---|---|
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 * | 6/2015 | Al-Ali .............. A61B 5/746 |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-Ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,554,737 | B2 | 1/2017 | Schurman et al. |
| 9,560,996 | B2 | 2/2017 | Kiani |
| 9,560,998 | B2 | 2/2017 | Al-Ali et al. |

(56) References Cited

U.S. PATENT DOCUMENTS

| | | |
|---|---|---|
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |

(56) References Cited

U.S. PATENT DOCUMENTS

| | | |
|---|---|---|
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| 11,147,518 B1 | 10/2021 | Al-Ali et al. |
| 2001/0018557 A1 | 8/2001 | Lynn et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0021678 A1 | 1/2007 | Beck et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0281838 A1* | 11/2009 | Lynn .................. G16H 50/70 705/3 |
| 2010/0004518 A1 | 1/2010 | Vo et al. |
| 2010/0030040 A1 | 2/2010 | Poeze et al. |
| 2010/0083968 A1* | 4/2010 | Wondka ............. G16H 50/30 128/204.23 |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |

(56) References Cited

U.S. PATENT DOCUMENTS

| | | |
|---|---|---|
| 2015/0080754 A1 | 3/2015 | Purdon et al. |
| 2015/0087936 A1* | 3/2015 | Al-Ali ............... A61B 5/0004 600/309 |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-All et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |

(56) References Cited

U.S. PATENT DOCUMENTS

| | | |
|---|---|---|
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |

FOREIGN PATENT DOCUMENTS

| | | |
|---|---|---|
| WO | WO 03/091932 | 11/2003 |
| WO | WO 2007/011930 | 1/2007 |
| WO | WO 2012/109671 | 8/2012 |

OTHER PUBLICATIONS

International Search Report and Written Opinion for PCT/US2012/024908 dated Jul. 20, 2012 in 14 pages.

* cited by examiner

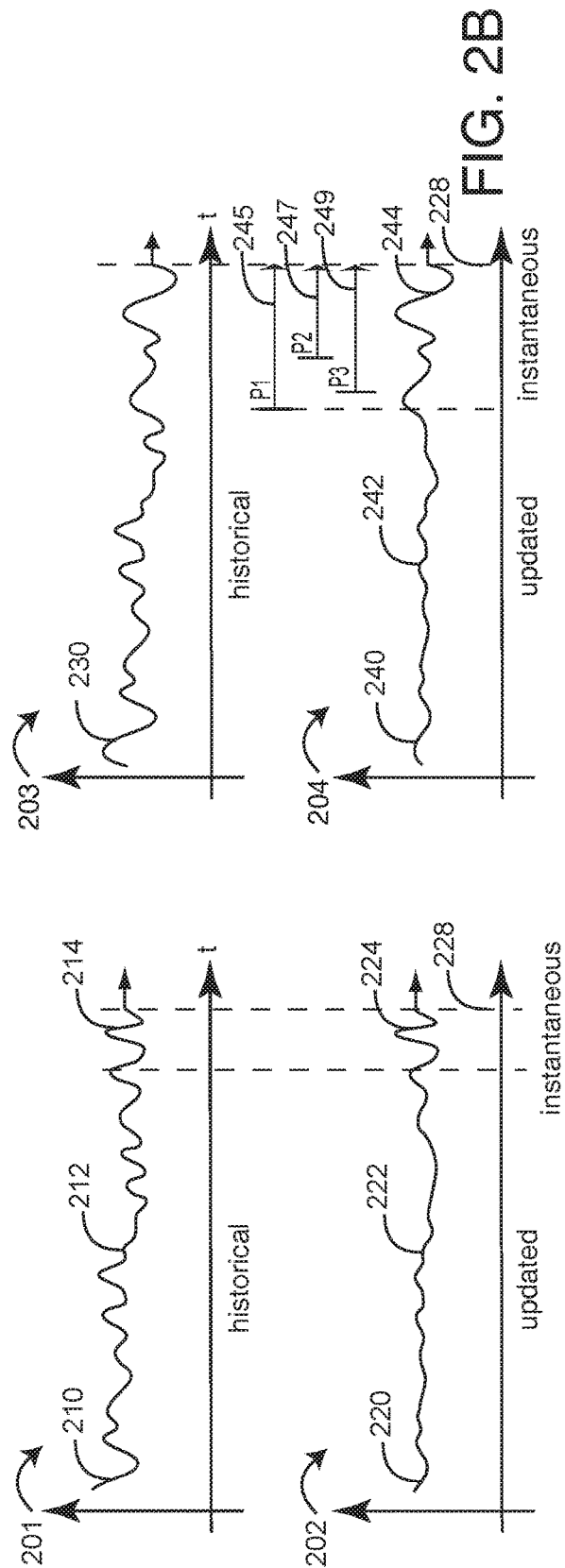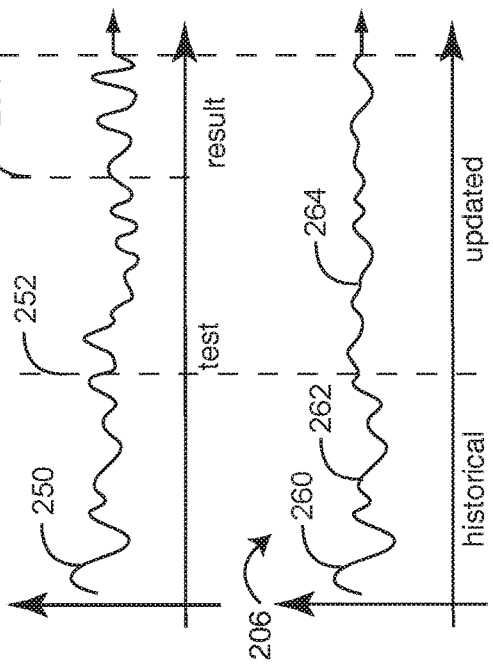

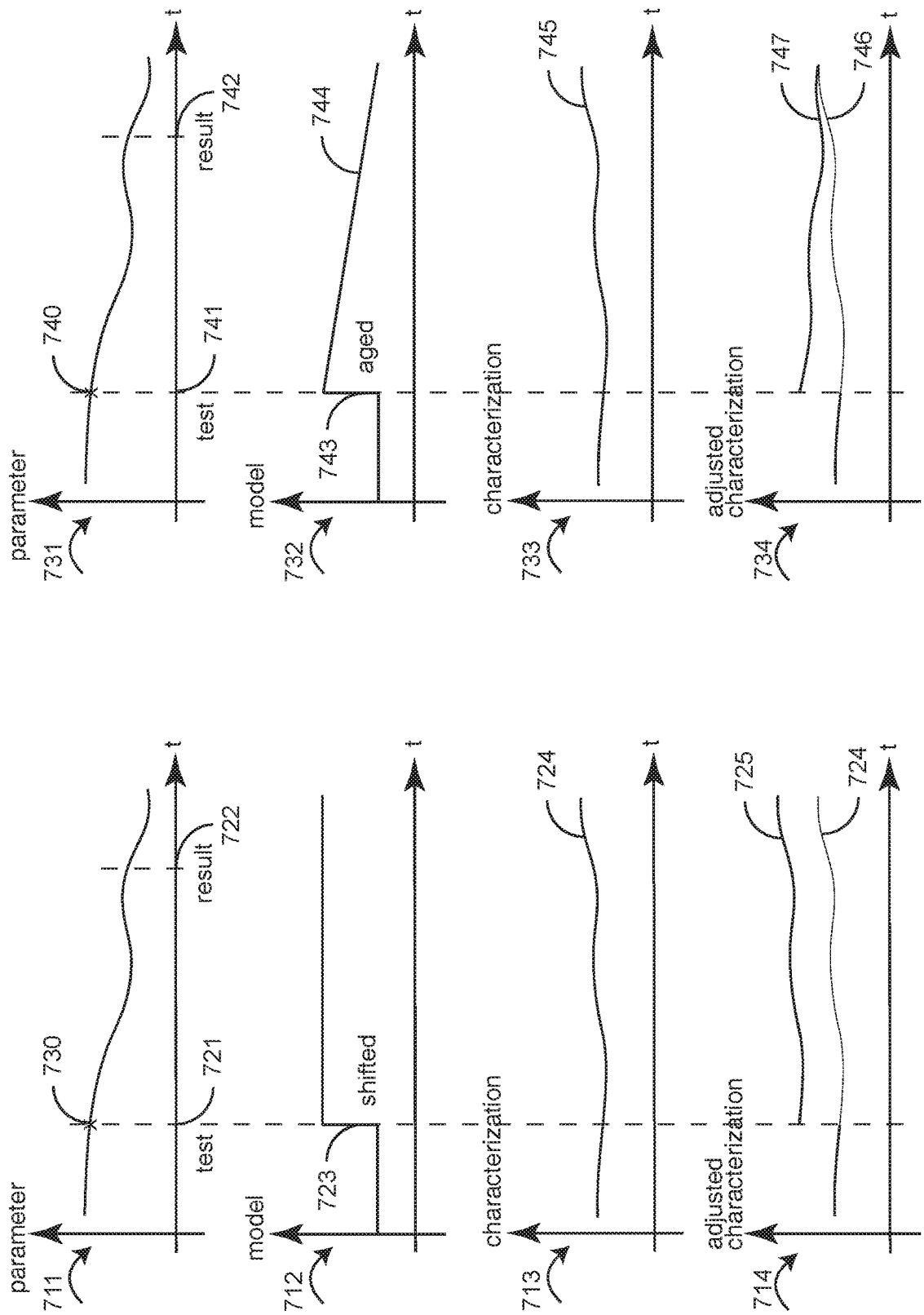

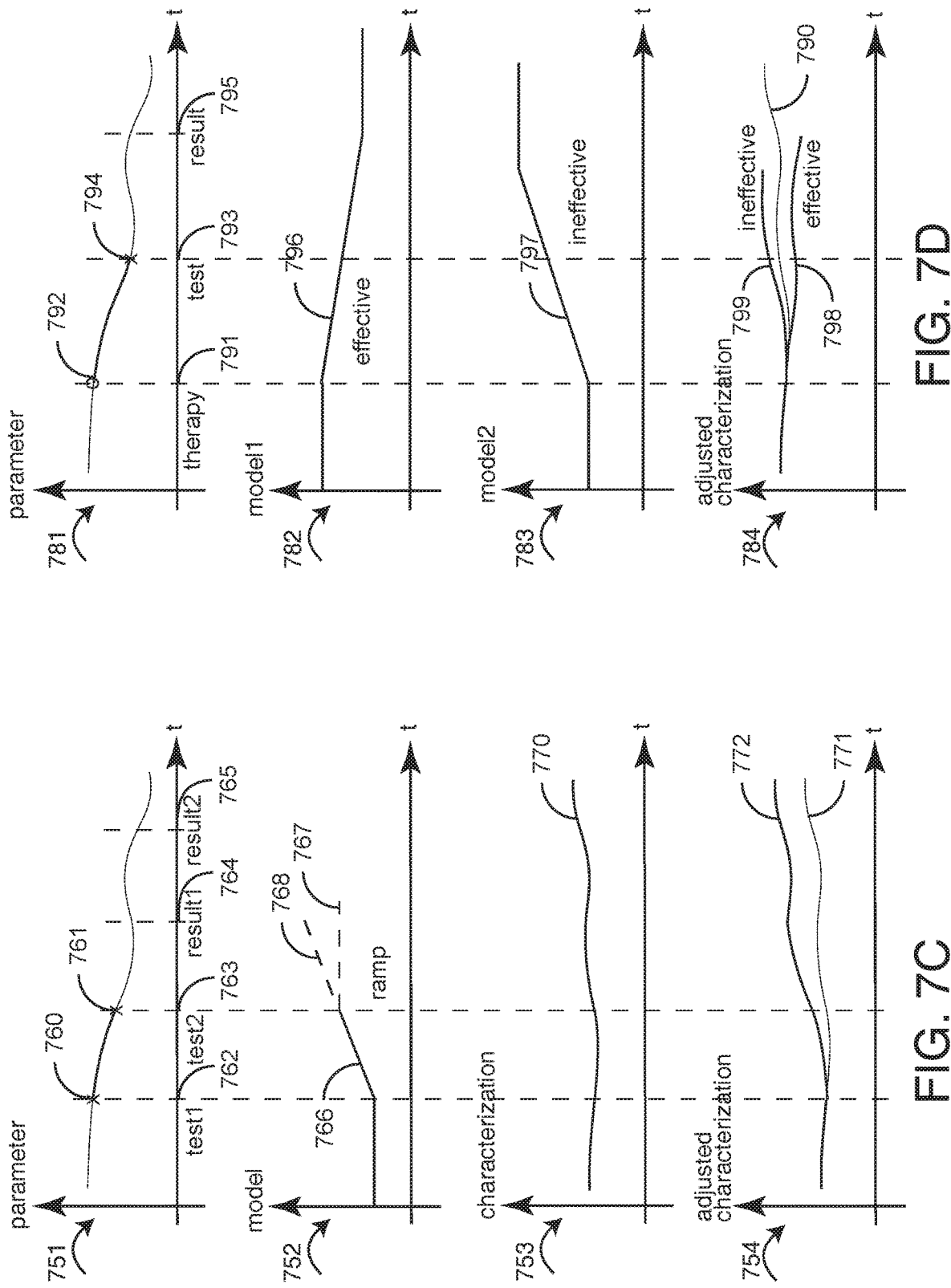

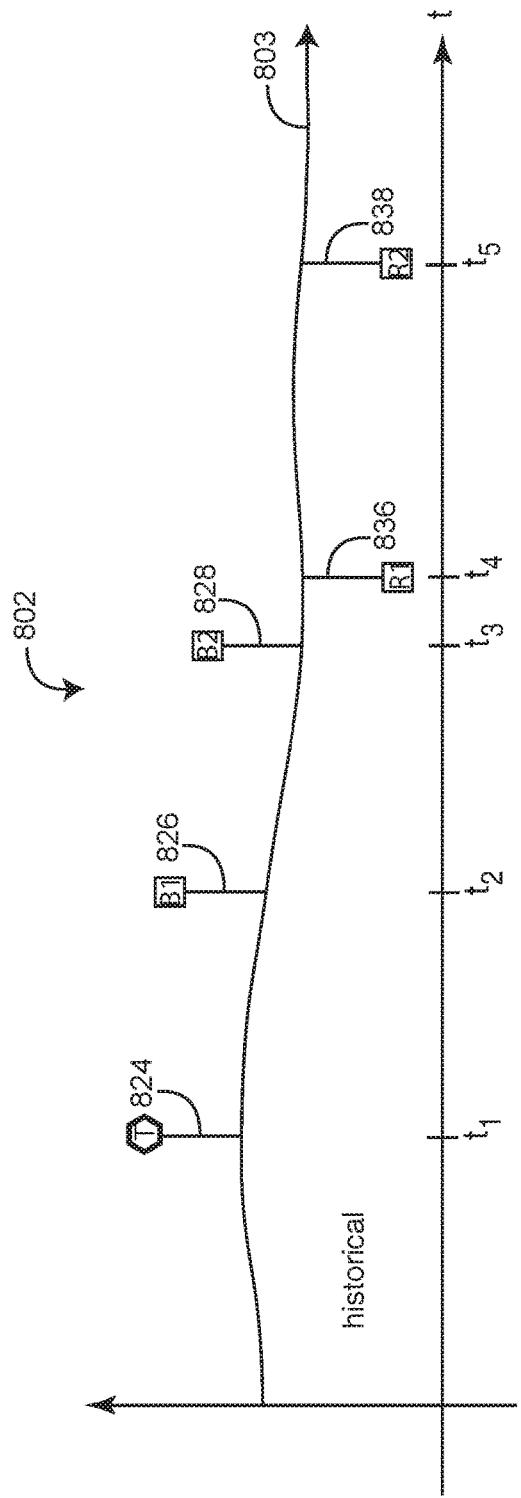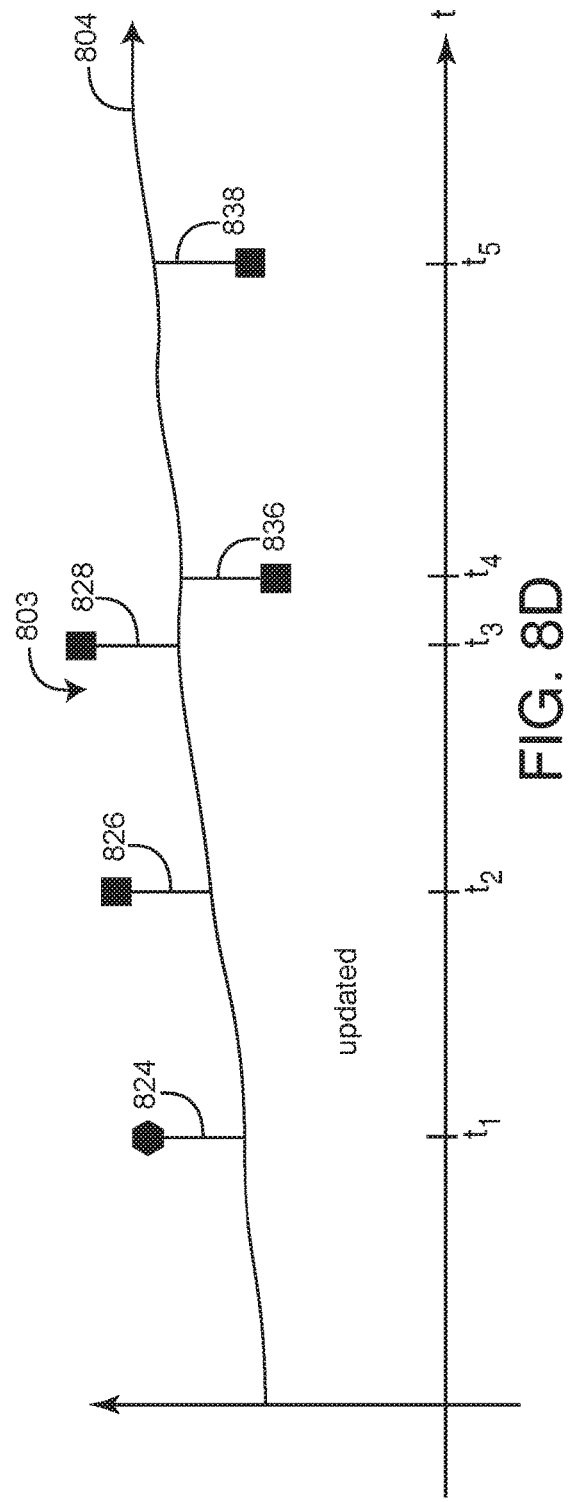
FIG. 8C
FIG. 8D

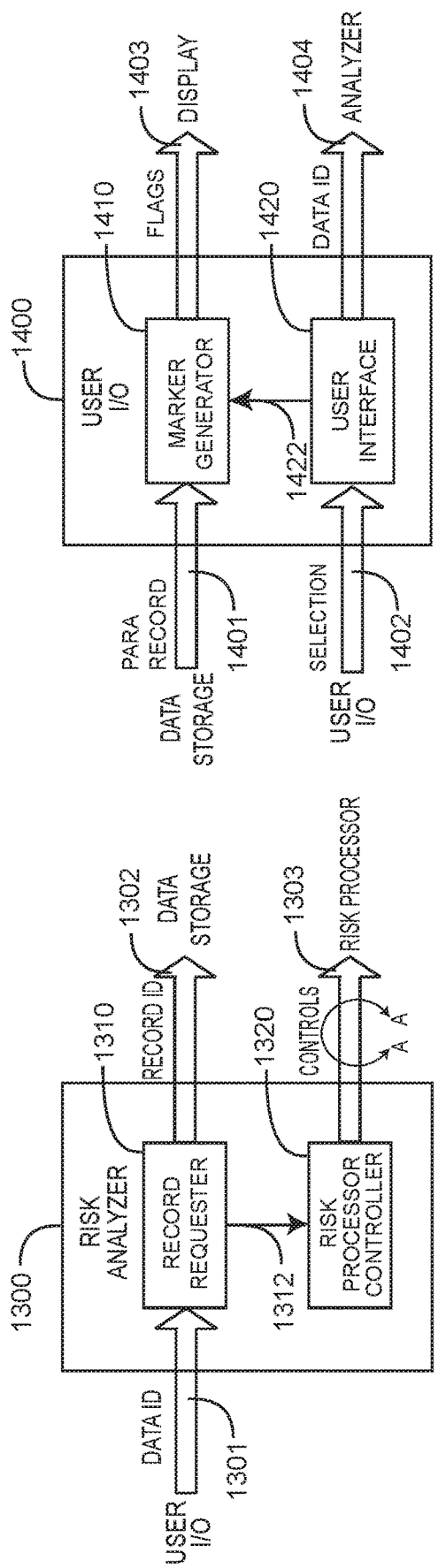
FIG. 14
FIG. 13
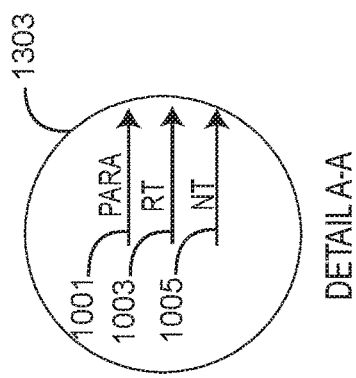
DETAIL A-A

MEDICAL CHARACTERIZATION SYSTEM

PRIORITY CLAIM TO RELATED PROVISIONAL APPLICATIONS

The present application claims priority benefit under 35 U.S.C. § 119(e) to U.S. Provisional Patent Application Ser. No. 61/442,264 filed Feb. 13, 2011, titled Complex System Characterizer hereby incorporated in its entirety by reference herein.

SUMMARY OF THE INVENTION

A typical multi-parameter patient monitoring system (MPMS) derives multiple medical-related parameters and displays the results as various combinations of readouts and waveforms. A MPMS is responsive to sensors attached to a patient and actively responds to the patient's physiology. Lacking, however, is the inclusion in patient monitoring of test measurements and other discrete data; previously recorded sensor data or parameters; and physiological data that has no particular time reference such as genetic information, family history and previous diagnoses, to name a few. Further, a MPMS does not provide a medical characterization of a patient that includes a time element associated with test measurements and other discrete data including the time a test is taken or the time span of a parameter recording. Further, MPMS information is not under dynamic user control so as to include or exclude information to determine overall impact on a patient characterization.

One aspect of a medical characterization system is configured to input medical-related continuous parameters and discrete data so as to calculate a characterization timeline indicative of a physiological condition of a living being. The medical characterization system has a parameter generator, a characterization processor, a discrete data source and a characterization analyzer. The parameter generator is in sensor communications with a living being so as to generate a continuous parameter. The characterization processor is responsive to the continuous parameter so as to generate a medical characterization of the living being as a function of time. The discrete data source provides a datum responsive to the living being at a first time and that is available to the characterization processor at a second time. A characterization analyzer enables the characterization processor to update the medical characterization in view of the datum as of the first time.

In various embodiments, the medical characterization system further comprises an analyzer model in communications with the characterization analyzer so as to determine the effect of the medical characterization update over time. The analyzer model comprises a selectable one of an upward shift, a downward aging and an upward ramp. A data storage is in communications with the data source and the characterization processor so that the characterization analyzer can selectively update past portions of the medical characterization with later data. An input/output interface allows a person to selectively control the medical characterization updates. In an embodiment, the input/output interface has a display navigation tool that displays a selectable test epoch at the first time and a corresponding result epoch at the second time. In an embodiment, the analyzer model is responsive to one of a therapy time epoch and a test time epoch in view of a result epoch.

Another aspect of a medical characterization system are parameters generated in response to sensors in communication with a person. A medical characterization is calculated from the parameters that is generally indicative of the physiological condition of the person. A medical test is performed on the person at a test time. The medical test result is received at a later result time. The medical characterization is updated according to the medical test result as of the test time.

In various embodiments, the medical characterization models the behavior of the medical characterization over time in response to the medical test as a test model. The medical characterization is displayed as a function of time. The test time and the result time are indicated on the display as a test and result epochs, respectively. At least one of the test epoch and the result epoch are selected by a user so as to initiate the updating. The test model is applied to the medical characterization as of the test time in response to the selecting. A therapy time is indicated on the display as a therapy epoch. The behavior of the medical characterization over time in response to a therapy is modeled as therapy effectiveness. A therapy time is indicated on the display as a therapy epoch. The therapy epoch is selected, and the therapy effectiveness model is applied to the medical characterization as of the therapy time in response.

A further aspect of a medical characterization system is an apparatus comprising a data source, a characterization processor and a characterization analyzer. The data source provides both a continuous parameter timeline and a discrete test result responsive to the medical state of a living being at a test time. The characterization processor is in communications with the data source so as to calculate a medical characterization of the living being according to each of the continuous parameter and the discrete test result. The characterization analyzer updates the continuous parameter timeline according to the discrete test result as of the test time.

In various embodiments, the characterization processor, a processor engine and a processor model. The characterization processor has an input selector that allows a user to select a current data input or a sync data input as a medical data output. The processor engine inputs the medical data and generates a medical characterization. The processor model determines how the medical characterization is calculated based upon the medical data. The characterization analyzer has an analyzer engine that combines current medical data and recalled medical data to generate sync data according to an analyzer model. A graphics generator outputs the medical characterization to a display. A marker generator indicates test and result epochs on the display in conjunction with the medical characterization. An analyzer model determines the effect of a test result on the medical characterization. The analyzer model further indicates the effectiveness of an earlier therapy based upon the test result.

Advantageously, a medical characterization system is configured to input real-time and non-real-time discrete and continuous medical-related parameters and data so as to calculate, in an embodiment, a risk timeline indicative of a probability of serious illness or death due to injury, disease or other physiological conditions. The risk timeline is dynamically updated over past time segments as well as present time to account for newly received or previously unused parameters and data. In an embodiment, the medical characterization system has a parameter generator in sensor communications with a patient so as to generate continuous data streams indicative of the patient's physiological condition. A risk processor responsive to the parameter generator generates a risk timeline. A risk analyzer controls the risk processor so as to modify the risk timeline over past time segments as well as present time according to new information regarding the patient, such as medical tests, diagnoses and therapies, to name a few. The risk analyzer relates this new information back to the time that the information originated. Further a medical characterization system advantageously allows a user to dynamically include or exclude individual parameters or data or selected groups of parameters and data so as to determine the impact on the risk timeline, both past and present.

Although an embodiment of a medical characterization system is described with respect to calculating and generating a dynamically adjustable medical risk characterization timeline, in other embodiments a medical characterization can reflect any of a variety of medical characteristics, both general and specific, such as wellness, fitness or competitive readiness of athletes, to name a few. Further, although an embodiment of a medical characterization system is described with respect to a single risk timeline, in other embodiments a medical characterization system can calculate and simultaneously display multiple characteristics concurrently. For example, in addition to or instead of an overall risk timeline, the characterization can be multiple particularized risk timelines, such as an array of risks to a person's circulatory, respiratory, neurological, gastrointestinal, urinary, immune, musculoskeletal, endocrine or reproductive systems.

DESCRIPTION OF THE DRAWINGS

FIGS. 2A-C are graphs of a medical characterization versus time, which generally illustrate medical characterization;

FIGS. 7A-D are graphs of exemplar analyzer models versus time;

FIGS. 8A-D are exemplar characterization versus time displays illustrating a navigation tool for analyzing medical characterizations;

FIG. 13 is a block diagram of a risk analyzer embodiment; and

FIG. 14 is a block diagram of an I/O interface embodiment.

DETAILED DESCRIPTION OF THE PREFERRED EMBODIMENTS

Figure 1:
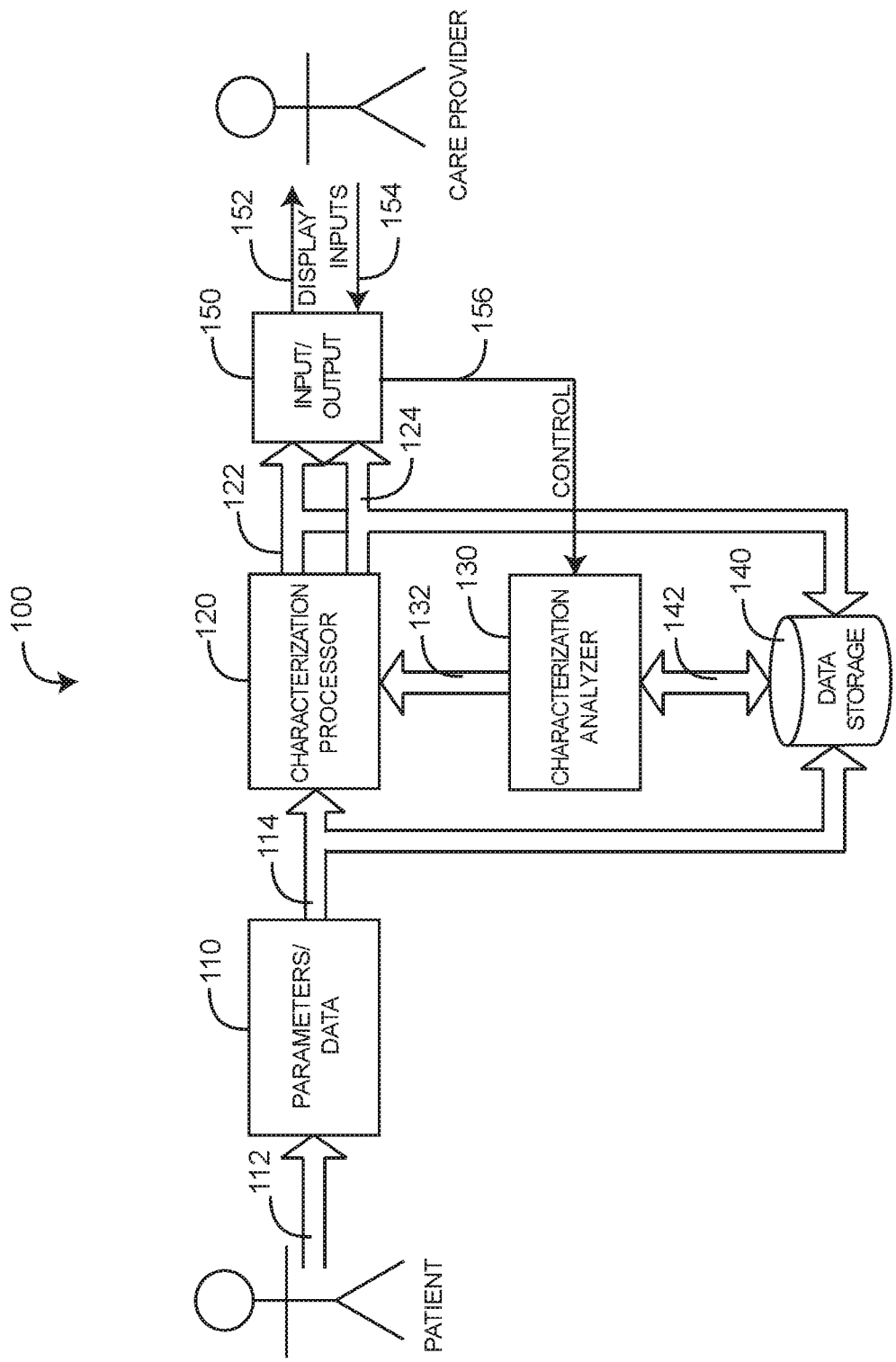
FIG. 1 is a general block diagram of a medical characterization system.

FIG. 1 generally illustrates a medical characterization system 100, which provides a medical characterization of a living being, such as a patient or person under medical care. The medical characterization system 100 has data sources 110, a characterization processor 120, a characterization analyzer 130, data storage 140 and I/O (input/output) 150.

Data sources 110 include various sensors and monitors in communications 112 with a patient so as to generate parameters or transmit data. Data sources 110 further include discrete data such as test results. As such, data sources 110 generally provide parameters, test data and other information 114 indicative of one or more aspects of the patient. The characterization processor 120 is responsive to the data sources 110 so as to derive a medical characterization 122. In an embodiment, the medical characterization is a wellness or a risk index. The characterization processor 120 also generates epochs 124 indicating discrete data, as described with respect to FIG. 4, below. The characterization analyzer 130 advantageously updates and synchronizes the characterization 122 so that it is accurate across all time periods of interest. Also, the characterization analyzer 130 generates different versions or realities of the medical characterization 122 based upon the inclusion or exclusion of available parameters and data 114. This advantageously allows a care provider or other user to determine the impact of that information 114 on the medical characterization 122.

FIGS. 2A-C generally illustrates functional aspects of a characterization analyzer 130 (FIG. 1). A characterization processor 120 (FIG. 1) generates an initial medical characterization 210 in response to data sources 110 (FIG. 1), which is illustrated in a medical characterization versus time graph 201 up to a present time 228. The characterization analyzer 130 (FIG. 1) in conjunction with the characterization processor 120 (FIG. 1) also generates one or more updated characterizations 220 in response to a data source 110. A particular updated characterization 220 may provide an updated portion 222 and retain a relatively instantaneous portion 224 of the initial characterization 210. In various embodiments, the updated portion 222 may extend to present time 228 such that the instantaneous portion 224 is negligible.

As shown in FIG. 2A, an initial medical characterization 210 may only be accurate as of the current time 228. As such, it is difficult for a care provider to accurately assess an individual's medical condition over a period of time based upon this information alone. In particular, the historical values 212 may well be out-of-date as more information about the individual is received. This is particularly true if newly received information is not instantaneous, i.e. pertains to a past time. The characterization analyzer 130 (FIG. 1) advantageously generates one or more updates of the initial medical characterization 210 over some or all of the characterization time record so as to take into account not only the patient history but also newly gained information that relates back in time. The characterization analyzer 130 (FIG. 1) generates one or more of these characterization updates 222 as the characterization processor 120 (FIG. 1) continues to provide instantaneous characterizations 210. Further, a medical characterizer system 100 (FIG. 1) embodiment has data storage 140 (FIG. 1) that advantageously records the initial characterization 210 and any or all subsequent updated characterizations 220 for playback so that the impact of newly received information may be reviewed and analyzed at the characterization processor output 122.

As shown in FIG. 2B, in a medical characterization versus time graph, an initial medical characterization 230 is generated by the characterization processor 120 (FIG. 1). In an exemplar embodiment, the medical characterization 230 incorporates several parameters P1, P2 and P3. However, P1 has a processing time t1 245, P2 has a processing time t2 247 and P3 has a processing time t3 249. If these processing times are not insignificantly short, the initial risk characterization 230 may not be accurate. In particular, the parameters P1-P3 may not be applicable to the present time 228, but rather relate back by the individual computation times 245-249. The characterization analyzer 130 (FIG. 1) advantageously calculates an updated characterization 242 that relates-back each parameter by its particular processing time 245-249. Accordingly, the updated characterization 240 has an updated portion 242 and an instantaneous portion 244, as generally described with respect to FIG. 2A, above. The updated portion 242 advantageously takes into account all parameter processing times 245-249. The instantaneous portion 244 may be ambiguous until the processing time issues are resolved.

As shown in FIG. 2C, an initial medical characterization 250 is generated by the characterization processor 120 (FIG. 1). At a specific time 252, a patient test is initiated. This may be a blood test, urinalysis, x-rays or physical exam to name just a few. At some later time 254, the characterization processor 120 (FIG. 1) receives the test results. However, the test results are not applicable to the time received 254 but rather to the test time 252. The characterization analyzer 130 (FIG. 1) in conjunction with the characterization processor 120 (FIG. 1) advantageously generate an updated medical characterization 264 having a historical portion 262 and an updated portion 264. The historical portion 262 remains unchanged from the initial characterization 250. The updated portion 264, however, advantageously relates the test result 254 back to the test time 252. As such, the updated characterization 264 provides a care provider an accurate representation of an individual's medical status, such as risk or wellness, to name a few. Further, the care provider can advantageously compare the initial 250 and updated 260 medical characterizations to determine the full impact over time of the test result 254 on the individual's status.

Figure 3:
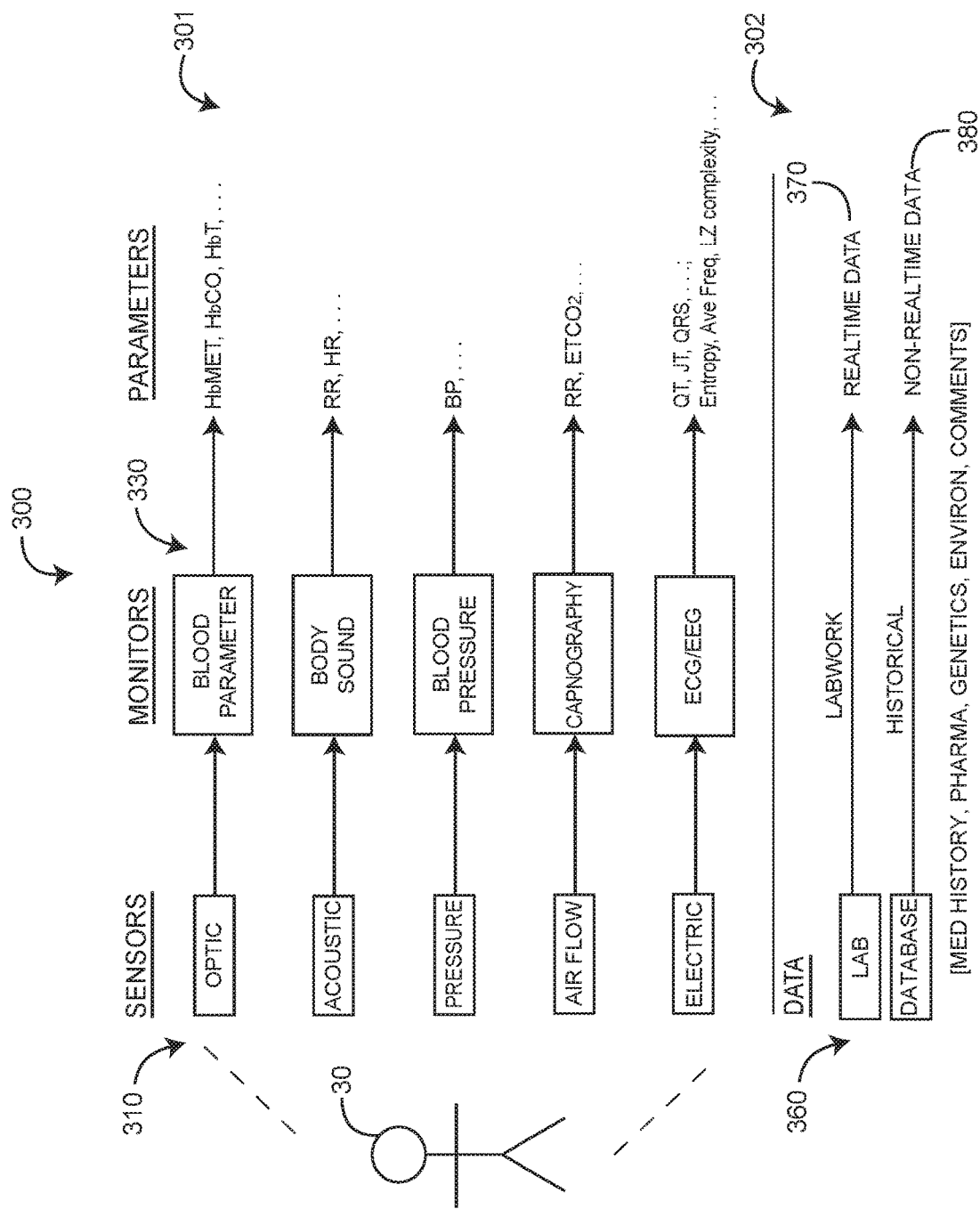
FIG. 3 is detailed block diagram of a medical data source embodiment.

FIG. 3 illustrates an exemplar medical data source 300 that is in communications with a living being such as a patient 30 so as to output information including parameters 301 and data 302 used to generate a medical characterization. One or more sensors 310 are in contact with the subject 30 so as to generate continuous physiological information, such as information that is a continuous function of time over a particular time segment and that regards the subject's physiological condition. One or more monitors 330 may be in communications with the sensors 310 so as to calculate parameters 301. Parameters 301 are typically realtime, continuous information generated from sensors 310 and corresponding monitors 330, or sensors 310 alone, and are accordingly immediately responsive (taking into account monitor processing times) to events occurring in realtime with the patient 30. Parameters 301 may also include segments of sensor 310 and monitor 330 outputs which are recorded on a variety of analog and digital devices including magnetic tape and disks, semiconductor memories and optical storage devices, to name a few examples, and played-back at a later time. Sensors 310 may include optical sensors, such as pulse oximetry sensors; acoustic sensors, such as piezoelectric devices; blood pressure sensors, such as an inflatable cuff incorporating an audio transducer; airflow sensors and electrodes, to name just a few. Monitors 330 may include pulse oximeters, advanced blood parameter monitors, acoustic monitors and capnography monitors, as examples. Recording devices may include specialty devices, such as a Holter monitor for recording an ECG signal, or any general data recording mechanism, such as semiconductor memory, magnetic disks, optical disks and the like.

Also shown in FIG. 3, one or more data sources 360 having medical-related information generate discrete information 302. The discrete information may be associated with a particular point in time (realtime data 370), or not associated with any particular point in time (non-realtime data 380). Realtime data 370 may include laboratory work, such as blood tests, urinalyses, X-rays or MRIs to name a few, which generate results that can relate back to respective test times. Non-realtime information 380 is typically gathered from a variety of sources and stored and accessed via one or more databases. Databases may range from a centralized database administered by a single organization/entity to a number of distributed and disparate databases administered by a variety of organizations/entities. Non-realtime data 380 may include a subject's 30 medical history and pharmacological, genetic and environmental data, for example, which are not associated with any particular time or date or are too remote in time to relate back to any realtime parameters of interest.

Figure 4:
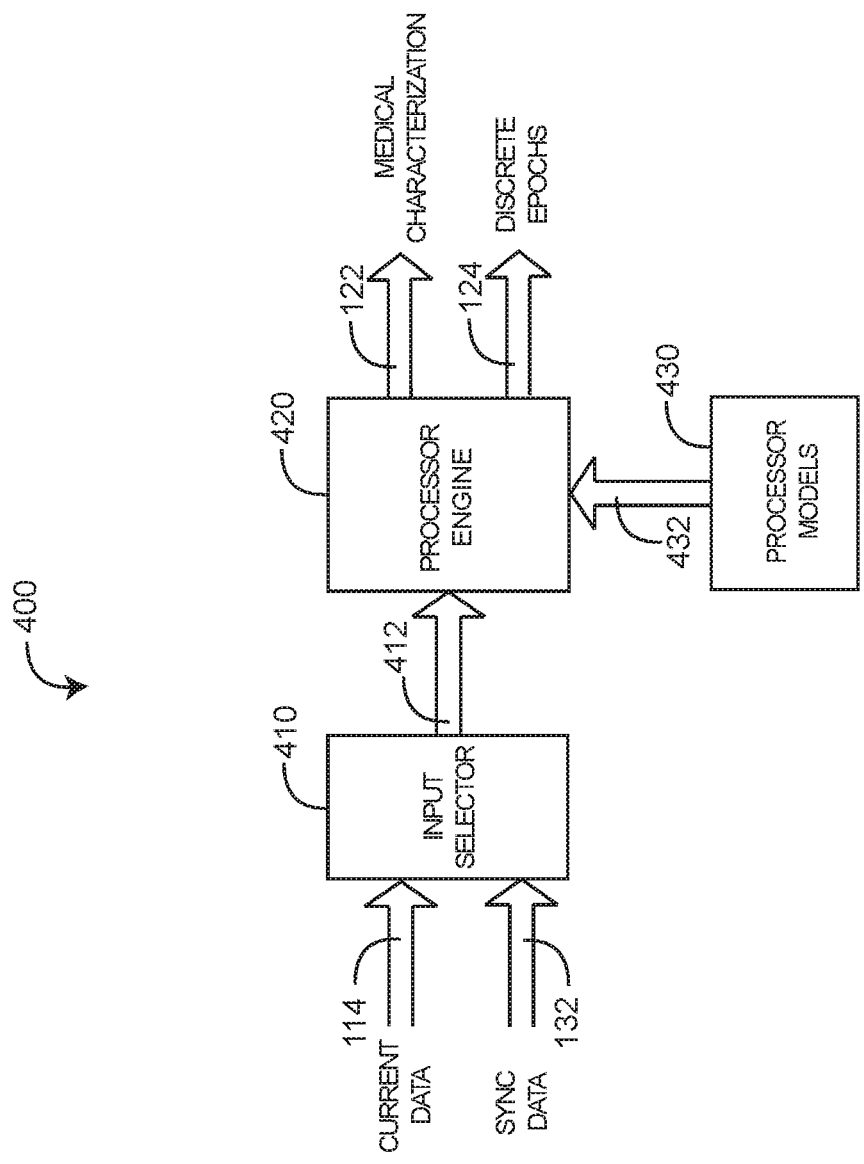
FIG. 4 is a detailed block diagram of a characterization processor embodiment.

FIG. 4 illustrates a characterization processor 400 embodiment having an input selector 410, a processor engine 420 and processor models 430. The input selector 410 allows a care provider or other user to select current medical data 114 including parameters derived from sensors and monitors and data derived from lab work and external databases. The input selector 410 also allows the care provider to select sync data 132 generated by the analyzer engine 510 (FIG. 5), as described below. In particular, the input selector 410 may generate a medical data 412 output to the processor engine 420 having current data 114 or sync data 132, which is a combination of current and recalled data. In this matter, a care provider may request a medical characterization 122 based upon current information, such as a blood test result, related back to the time the blood was drawn. This advantageously allows the blood test to be synchronized with parameters and other medical data at the time blood was drawn as opposed to the potentially much later time when the blood was tested and the test results were made available. This back-in-time synchronization of new results with recalled data is described in further detail with respect to FIGS. 7-8, below. Further, a care provider can generate multiple characterizations of various combinations of current data 114, including or excluding various parameters or tests, say, so as to determine the effect on the medical characterization 122.

Also shown in FIG. 4, processor models 430 determine what medical characterization 122 is derived and how the derivation is calculated. In an embodiment, the medical characterization 122 is a risk parameter, which advantageously provides a care provider with a real-time index indicative of, in one embodiment, the physiologic deterioration in a patient. A risk characterization is described in further detail with respect to FIGS. 9-14, below. Risk model embodiments for deriving a risk characterization are described with respect to FIGS. 11-12, below.

Figure 5:
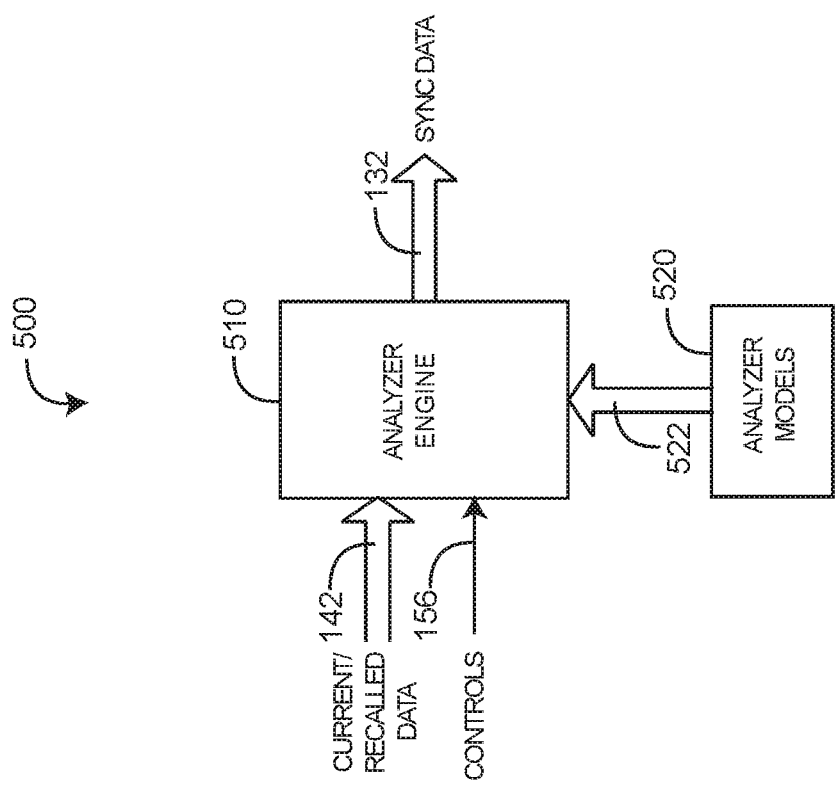
FIG. 5 is a detailed block diagram of a characterization analyzer embodiment.

FIG. 5 illustrates a characterization analyzer 500 embodiment having an analyzer engine 510 and analyzer models 520. The analyzer engine 510 inputs current and recalled data 142 so as to generated a synchronized (sync) data 132 output. Sync data 132 represents the time synchronization of current (new) data 114 (FIG. 1) with recalled (older) data 142 (FIG. 1), where, for example, the current data is used to update the recalled data so as to advantageously match a test result received at a later time with medical data generated when the test was taken. Such data synchronization is described in further detail with respect to FIGS. 8A-D, below. The analyzer models 520 determine the manner in which current data is combined with recalled data. Various analyzer models are described with respect to FIGS. 7A-D, below.

Figure 6:
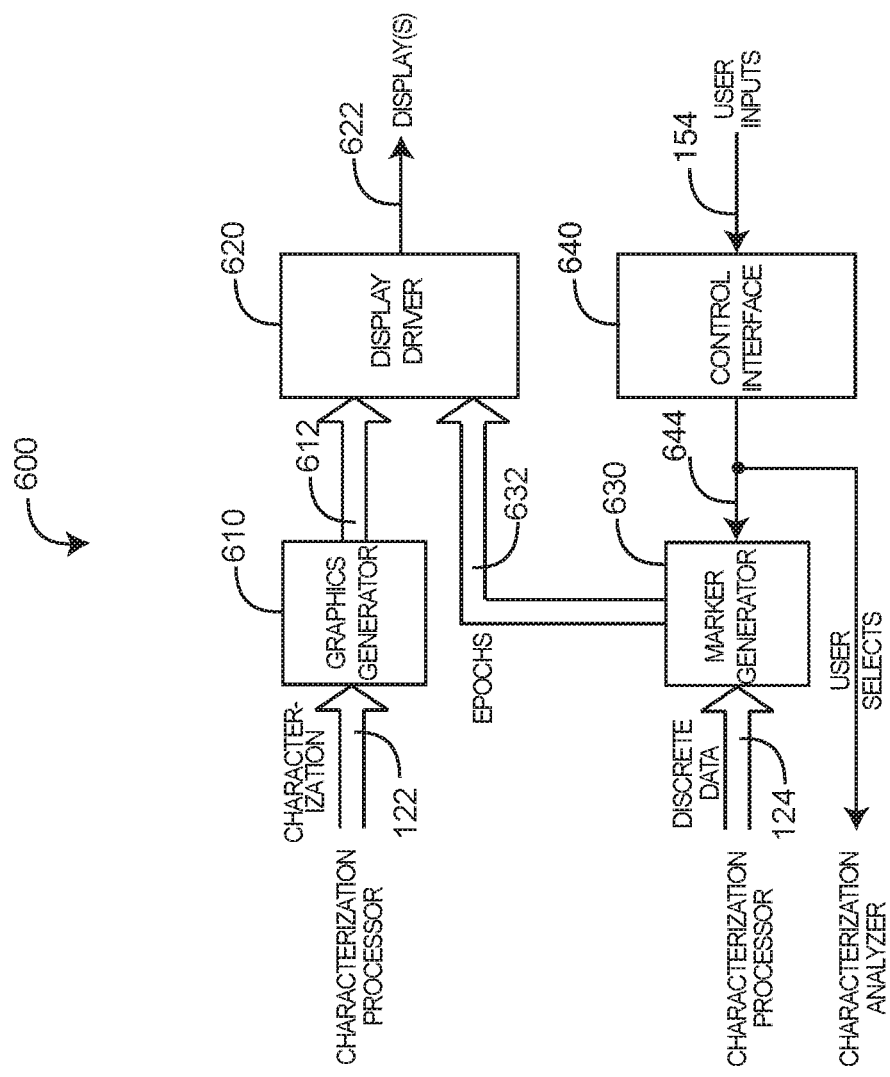
FIG. 6 is a detailed block diagram of an input/output (I/O) interface embodiment.

FIG. 6 illustrates an input/output (I/O) 600 embodiment having a graphics generator 610, a display driver 620, a marker generator 630 and a control interface 640. Generally, the I/O 600 inputs characterizations 122 and discrete data 124 from the characterization processor 122, which are graphically displayed 622 via the display driver 620. In particular, the graphics generator 610 outputs a characterization curve 612 interspersed with discrete variable epochs 632, as described below with respect to FIGS. 8A-B. The display driver 620 generates a display output 622 to any of various standard displays, such as a flat screen monitor, so as visually present the combined characterization curve 612 and epochs 632 to a care provider or other user. The care provider selects one or more epochs 632 via controls 154, such as a keypad, mouse or trackball, to name a few. The control interface generates user selects 644 in response to the controls 154. The marker generator 630 is responsive to the user selects 644 to mark the selected epochs 632, which also notifies the characterization analyzer accordingly.

FIGS. 7A-D illustrate exemplar characterization analyzer models. As described with respect to FIG. 5, above, a characterization analyzer advantageously time synchronizes previously known medical information with updated medical information so that a characterization processor may accurately derive and display a medical characterization of a patient for evaluation by a care provider. An advantageous aspect of characterization analysis is the accurate modeling, analysis and display of a medical characterization so as to compensate for the time delay between a data measurement and a data result, as generally described with respect to FIGS. 2A-C, above.

FIG. 7A graphs a parameter 711, a shift model 712, a medical characterization 713 and an adjusted medical characterization 714. The parameter graph 711 depicts a parameter measurement 730 at a test time 721 yielding a result at a result time 722. The model graph 712 depicts a medical characterization modeled as a step change or shift in the characterization 723 at the test time 721. The characterization graph 713 depicts a medical characterization 724 based upon the parameter 711 before the result 722 is known. The adjusted characterization graph 714 depicts the medical characterization before 724 and after 725 the modeled shift 723. For example, the parameter 711 may be Hb. The test may be a blood draw indicating an abnormally low hemoglobin. The characterization 713 and adjusted characterization 714 may be medical risk (see FIGS. 9-14, below), so as to indicate a step change in risk 724, 725 at the time of the test 721 as compared with the time of the test result 722.

FIG. 7B graphs a parameter 731, an aging model 732, a medical characterization 733 and an adjusted medical characterization 734. The parameter graph 731 depicts a parameter measurement 740 at a test time 741 yielding a result at a result time 742. The model graph 732 depicts a medical characterization modeled as an aging, i.e. a step change or shift in the characterization 743 at the test time 741 followed by a decreasing change 744 over time. The characterization graph 733 depicts a medical characterization 745 based upon the parameter 731 before the result 742 is known. The adjusted characterization graph 734 depicts the medical characterization before 746 and after 747 the modeled aging 743, 744. For example, the parameter 731 may be body temperature. The test may be a white blood cell count blood draw indicating a possible infection. The characterization 733 and adjusted characterization 734 may be medical risk so as to indicate an initial increase in risk 746, 747 at the time of the test 741, which diminishes over time as the result of known treatments or the fact that the test result becomes old and increasingly unreliable over time.

FIG. 7C graphs a parameter 751, a ramp model 752, a medical characterization 753 and an adjusted medical characterization 754. The parameter graph 751 depicts parameter measurements 760, 761 at a test times 762, 763 yielding results at result times 764, 765. The model graph 752 depicts a medical characterization modeled as a ramp-up 766, i.e. an increasing characterization at test time 762 that levels off 767 at test time 763 or continues to increase 768. The characterization graph 753 depicts a medical characterization 770 based upon the parameter 751 before the results 764, 765 are known. The adjusted characterization graph 754 depicts the medical characterization before 771 and after 772 the modeled ramp 766, 767. For example, the parameter 751 may be blood pressure. The test may be blood draws indicating Hct levels are decreasing over time. The characterization 753 and adjusted characterization 754 may be medical risk so as to indicate an increasing risk 771, 772 over time 762, 763.

FIG. 7D graphs a parameter 781, an effectivity model 782, a medical characterization 783 and an adjusted medical characterization 784. The parameter graph 781 depicts therapy 792 applied at a time 791 and a follow-up test 794 at a time 793 with a result at time 795. A first model graph 782 depicts a medical characterization modeled as an characterization decrease 796 over time, which depicts an effective therapy based upon the test results 795. A second model graph 783 depicts a medical characterization modeled as an characterization increase 797 over time, which depicts an ineffective therapy based upon the test results 794. The characterization graph 784 depicts a medical characterization 790 based upon the parameter 781 before the result 795 is known. The adjusted characterization graphs 798, 799 depict the medical characterization applied at the time of the therapy 791, assuming an effective 798 or ineffective 799 therapy, respectively. For example, the therapy may be administration of antibiotic and the test may be throat culture. Advantageously, the various models allow a medical characterization, such as risk, to be accurately reflected as of the time of a test or as of the time of an applied therapy, as examples. Further, the models advantageously allow the medical characterization to be modeled back in time in a variety of ways depending on the parameter measured, the type of test, the number of tests and therapies applied. These models may variously reflect characterization shifts, aging, ramps as examples. In other embodiments, multiple tests may allow a characterization model to be a parametric curve depending on the test times and results.

Figure 8A:
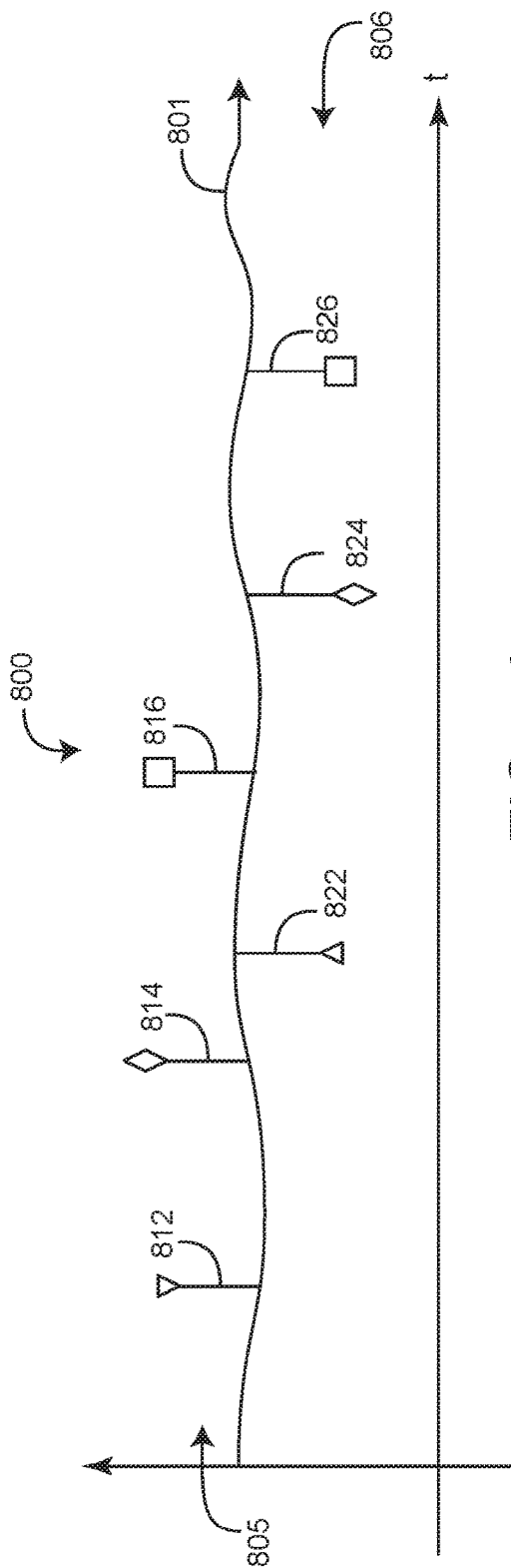
Figure 8B:
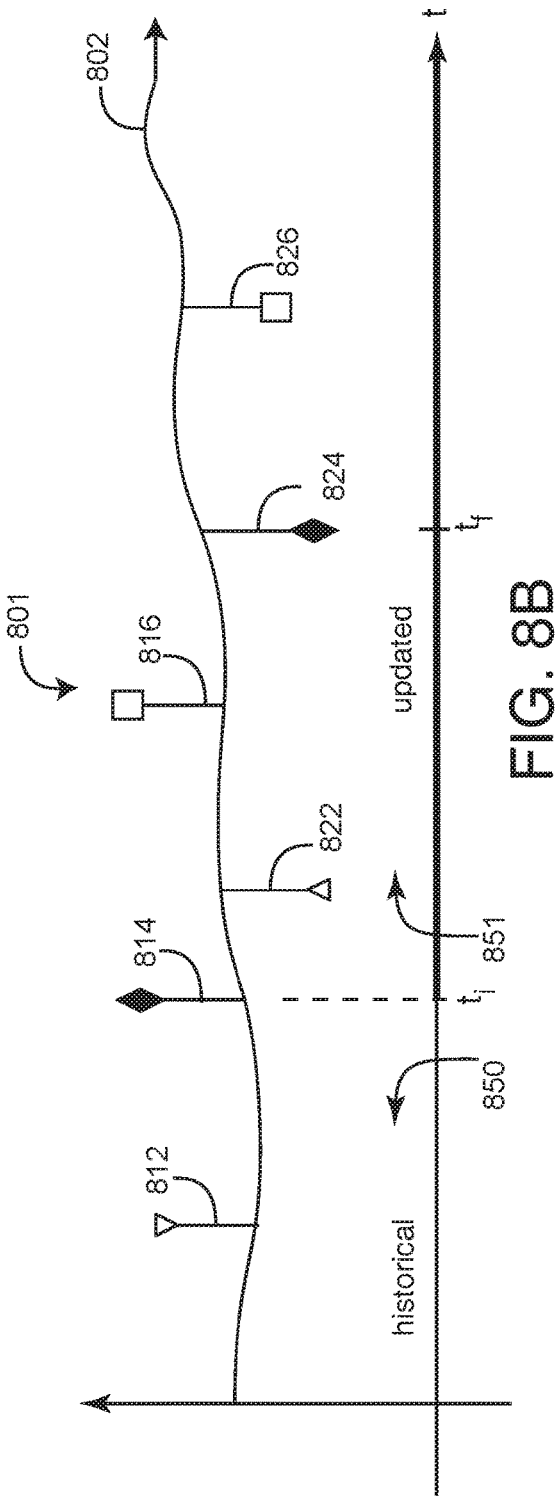

FIG. 8A-B illustrates a display navigation tool (DVT) 800 that user I/O 150 (FIG. 1) generates on a user display 152 (FIG. 1). The DVT advantageously allows a care provider or other user to selectively control the incorporation of test data into a medical characterization of a patient or other living being. In particular, a characterization processor 120 (FIG. 1) generates a characterization 122 output, which is viewed as a characterization 801 timeline on the user display. Advantageously, user I/O superimposes discrete test epochs 812-816 and corresponding result epochs 822-826 on the characterization 801 timeline so that a user can selectively incorporate discrete test data into characterization calculations. In an embodiment, the characterization is a measure of risk.

As shown in FIG. 8A, in a particularly advantageous embodiment, test and result epochs 805, 806 are displayed as paired flags. A first set of flags 805 indicate tests and a second set of flags indicate results. In an embodiment, the test flags 805 extend above the characterization 801 timeline and result flags 806 extend below the characterization 801 timeline. In this manner, a user viewing the display can readily determine the time a test occurs and the time a corresponding result is received. In an embodiment, test/result pairs (e.g. 812/822; 814/824 and 816/826) are shown with unique matching flags so that a user viewing the display can readily determine matching pairs and distinguish them from other matching pairs.

As shown in FIG. 8B, a selected test flag 814 and corresponding test result flag 824 are indicated on the display by bolding, coloring or otherwise highlighting the flag pair 814/824. Once a particular pair is selected, a user can initiate a characterization recalculation, as described with respect to FIGS. 1-7, above. The characterization recalculation modifies the characterization timeline to account for the test data, and this modification relates back to the test epoch. A corresponding characterization recharacterization 802 timeline is displayed, where the test result 824 at time $t_f$ relates back to the test time $t_i$. The characterization recharacterization generates an updated characterization 851 timeline portion and a historical (unchanged) characterization 850 timeline portion.

In an embodiment, a user temporarily positions a cursor (via a mouse or other pointing device) over a test or result so as to trigger a pop-up that provides a written description of the test or result. The description may indicate the kind of test (e.g. blood analysis, x-ray, urinalysis, etc.); the time and date of the test and result; the test source, such as a specific laboratory; and the physician in charge, to name just a few. Multiple test/result pairs may be selected so as to allow a user to see the impact on the characterization of multiple groups of tests. In other embodiments, not shown, non-realtime data including personal history (e.g. smoking, alcohol or drug abuse); medical history (e.g. cancer, heart disease, congenital defects); family history; personal genome data, among many others, are listed on demand and selectable individually or in groups so as to recharacterize risk accordingly.

As shown in FIG. 8C, in a particularly advantageous embodiment, multiple related test and result epochs 824-838 are displayed with matching flags and can be simultaneously selected so as to trigger multi-point characterization models relating back to multiple tests 824, 826. As shown in FIG. 8D, a selected set of therapy and test flags 832-836 and corresponding result flags 836, 838 are indicated on the display by bolding, coloring or otherwise highlighting the flag sets 832/834/836. Once a particular set is selected, a user can initiate a characterization recalculation, as described with respect to FIGS. 7A-D, above. The characterization recalculation modifies the characterization timeline to account for the therapy and/or test data, and this modification relates back to a therapy or test epoch. A corresponding recharacterization 804 timeline is displayed, where the test result 836 at time $t_4$ relates back to a test time $t_2$, a therapy time $t_1$ or a combination of test or therapy times.

Figure 9:
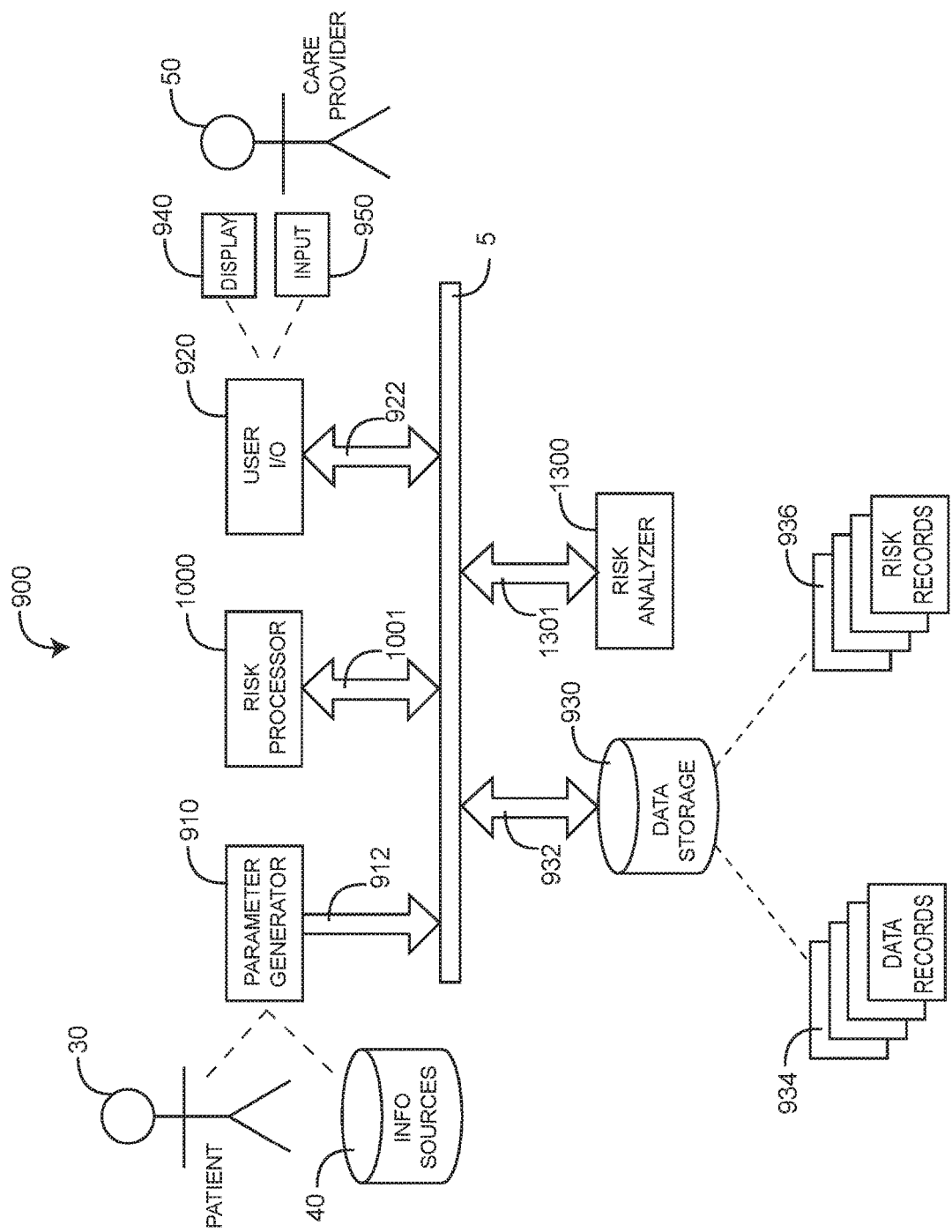
FIG. 9 is a detailed block diagram of a risk characterization system embodiment.

FIG. 9 illustrates a medical risk system 900 embodiment of a medical characterization system. Generally, the medical risk system 900 characterizes a person with respect to their physiological wellness or illness. In an embodiment, the medical risk system 900 advantageously indicates a potential for near-term serious physiological impairment or death due any one or more of disease, injury, surgical complications, drug side-effects or allergic reactions, to name just a few.

As shown in FIG. 9, medical risk system 900 has a parameter generator 910, a risk processor 1000, user input/output 920, data storage 930 and a risk analyzer 1000 all communicating over a common network 5. Generally, the parameter generator 910 is in communications with a patient 30 and various information sources 40 regarding the patient so as to generate parameters and data 912 (collectively "medical data") indicative of a patient's medical state. This data 912 is stored as one or more records 934 in the data storage 930. The risk processor 1000 is responsive to the data 934 so as to generate a risk 1001 output, indicative of the patient's medical risk. Risk 1001 is stored as one or more risk records 936 in the data storage 930. In an embodiment, risk 1001 is a function of time having a high value if a person is at a high risk of an impeding serious or life-threatening physiological event and a low value if a person has a correspondingly low risk of such an event. In an embodiment, the risk processor 1000 functions in conjunction with the risk analyzer 1300 to update risk records 936 with new data 912 so as to generate additional risk records 936, as described with respect to FIGS. 10-14, below. User I/O 920 allows doctors, medical staff, researchers and other care providers 50 to review and accurately modify risk records 936, to assess the impact on medical risk of newly obtain patient data 912 and to control the functions of the risk processor 1000 and risk analyzer 1300.

A wellness analysis system that integrates real-time sensor data from a patient or other subject regarding the status of any or all of a subject's circulatory, respiratory, neurological, gastrointestinal, urinary, immune, musculoskeletal, endocrine and reproductive systems and non-real-time information regarding the subject such as a lab work, pharmaceuticals and medications, medical history, genetics and environment from hospital records and other databases so as to generate a current or predictive wellness index or related output is described in U.S. patent application Ser. No. 13/009,505, filed Jan. 19, 2011, titled Wellness Analysis System, assigned to Masimo Corporation, Irvine Corporation ("Masimo") and hereby incorporated by reference herein. A risk analysis system that inputs sensor data from a subject, derives corresponding physiological parameters, assesses parameter risks according to parameter values and the impact those values have on the subject's physiology and estimates a total risk from a combination of the parameter risks, where total risk is a numerical indication of the likelihood of serious illness or debilitation or, in contrast, the likelihood of wellness or health is described in U.S. patent application Ser. No. 13/269,296, filed Oct. 7, 2011, titled Risk Analysis System, assigned to Masimo and hereby incorporated by reference herein.

Figure 10:
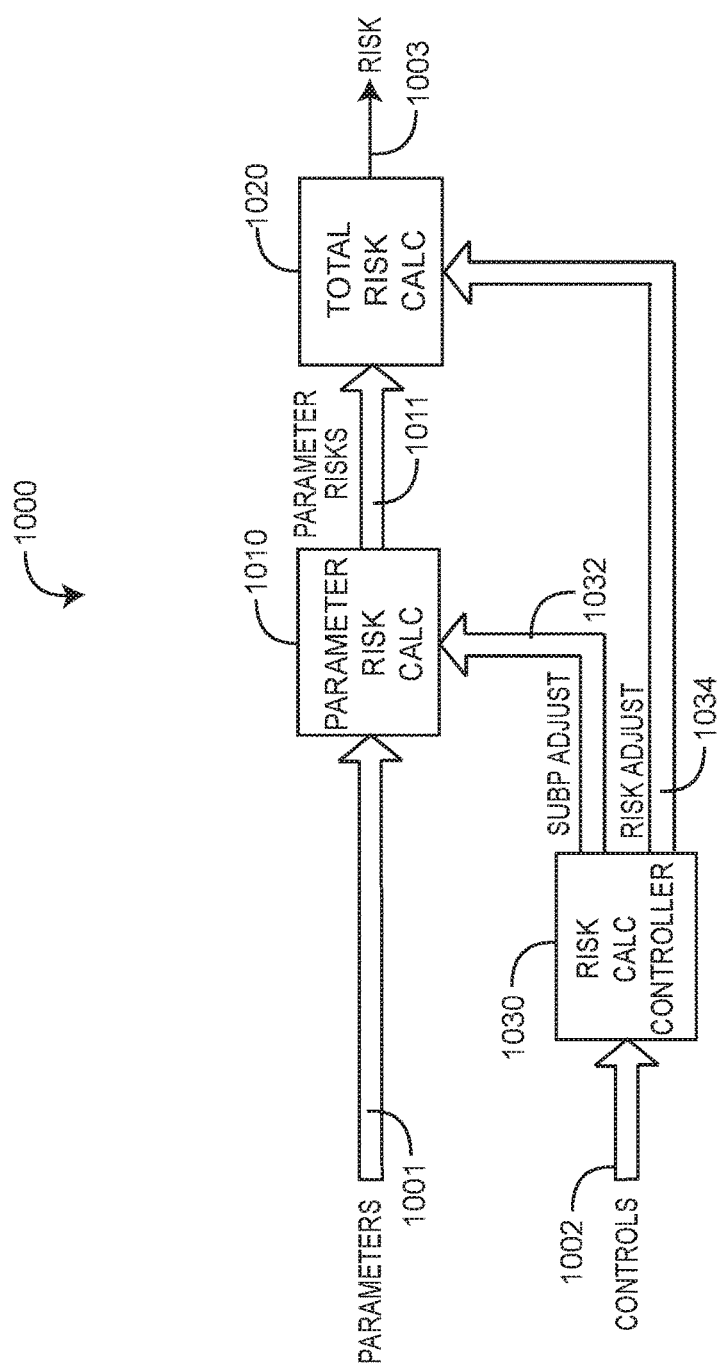
FIG. 10 is a flow diagram of a risk processor embodiment.

FIG. 10 illustrates a medical risk processor 1000 embodiment having input parameters 1001 and generating a risk 1003 output. The risk processor 1000 has a parameter risk calculator 1010, a total risk calculator 1020 and a risk calculation controller 1030. The parameter risk calculator 1010 inputs parameters 1001 and generates corresponding parameter risks 1011. The total risk calculator 1020 inputs the parameter risks 1011 and generates the risk 1003 output. The risk calculation controller 1030 advantageously modifies the parameter risks 1101 and the risk 1003 in response to controls 1002 from the risk analyzer 1000 (FIG. 10). Controls 1024 allow the risk analyzer 1303 (FIG. 13) to dynamically modify risk 701 in response to changes in the monitored parameters, new test results or data updates pertaining to the subject monitored.

As shown in FIG. 10, controls 1002 may indicate which parameters 1001 are active, what discrete real-time data, such as lab work, is available and what non-real-time data, such as medical history, is available. The risk calculation controller 1030 responds to the controls 1002 so as to generate sub-parameter adjusts 1032 to the parameter risk calculation 1010, as described with respect to FIG. 11, below. The risk calculation controller 1030 also responds to the controls 1002 so as to generate risk adjusts 1034 to the total risk calculation 1020, as described with respect to FIG. 12, below.

Figure 11:
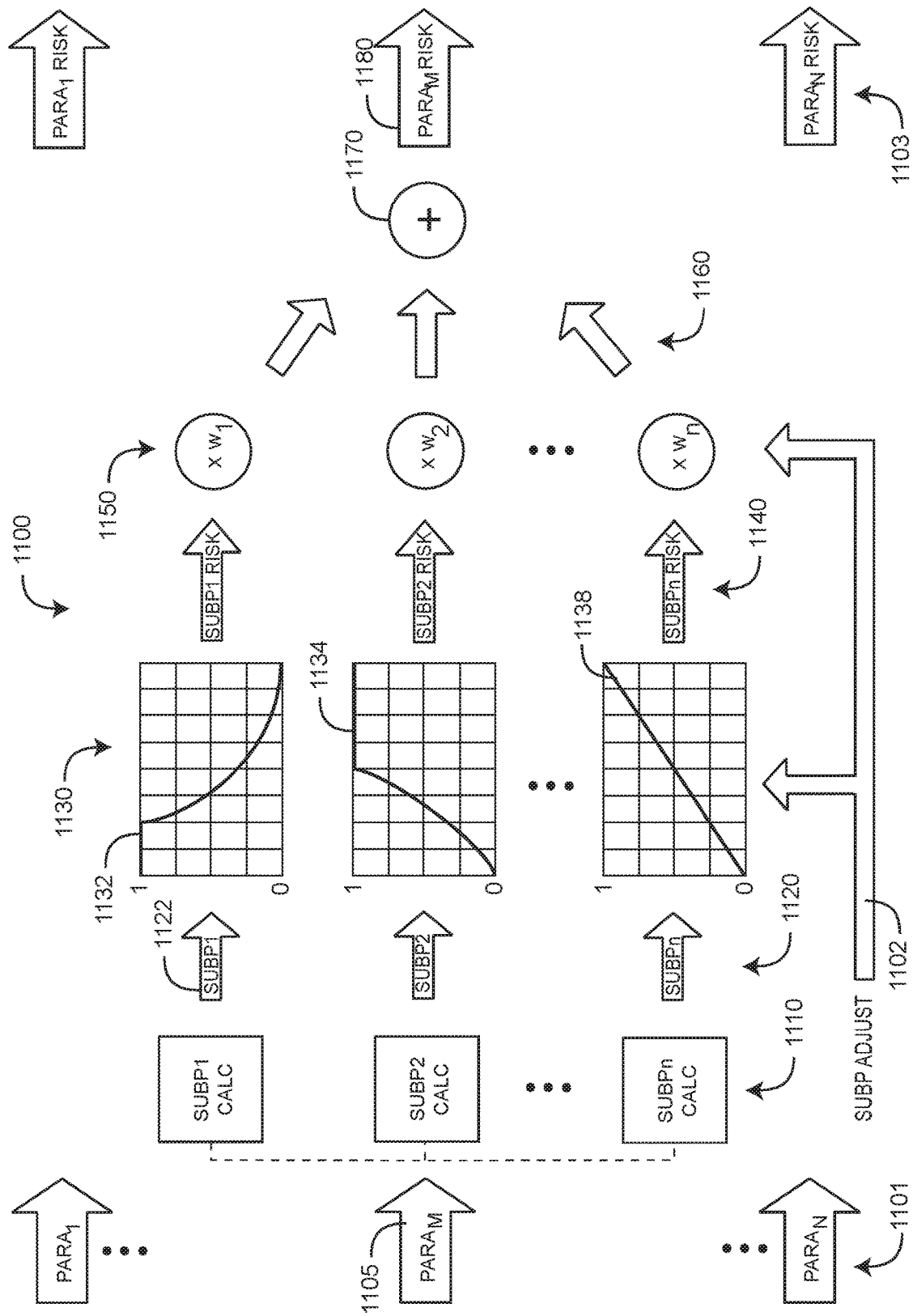
FIG. 11 is a flow diagram of a subparameter risk calculator embodiment.

FIG. 11 illustrates a parameter risk calculator 1100 having input parameters $PARA_1$-$PARA_N$ 1101 and output parameter risks $PARA_1$ RISK-$PARA_N$ RISK 1103. Each of the parameter risks 1103 is calculated independent of the others. Detailed in FIG. 11 is a risk calculation for $PARA_M$ 1105, which yields $PARA_M$ RISK 1180. Initially, sub-parameter calculators 1110 factor $PARA_M$ 1105 into a corresponding set of sub-parameters $SUBP_1$-$SUBP_n$ 1120. In particular, the sub-parameters calculators 1110 are each responsive to a particular feature of the parameter 1105. Generally, these features are chosen so that the corresponding sub-parameter risks $SUBP_1$ RISK-$SUBP_n$ RISK 1140, as a set, are representative of the risk associated with the particular input parameter $PARA_M$ 1105. For example, an oxygen saturation parameter might be factored into the sub-parameters saturation baseline, saturation instability and saturation average slope.

As shown in FIG. 11, sub-parameter risk calculators 1130 derive sub-parameters risks 1140 from the sub-parameters 1120. A sub-parameter risk calculator 1130 is a risk versus parameter value function (illustrated graphically herein). Accordingly, each sub-parameter risk calculator 1130 converts sub-parameter 1120 values into risks ranging between 0 to 1 (0% to 100% risk) according to the physiological characteristic represented by that sub-parameter 1120. For example, according to a risk function 1132, $SUBP_1$ 1122 has a maximum risk of 1 for a range of low values, and this risk decreases in inverse proportion $SUBP_1$ as $SUBP_1$ 1122 increases, eventually approaching 0 risk at the highest $SUBP_1$ values.

Further shown in FIG. 11, the sub-parameter risks 1140 are then weighted 1150 to yield weighted sub-parameter risks 1160, which are summed 1170 to yield the parameter risk $PARA_M$ RISK 1180. In an embodiment, the sub-parameter risk weights 1150 add to a value of 1. Accordingly, the weighted sub-parameter risks 1160 sum to a maximum value of 1, and $PARA_M$ RISK 1180 also varies between 0 to 1 (0% to 100% risk).

Additionally shown in FIG. 11, the sub-parameter risk calculators 1130 and the sub-parameter risk weights 1150 are dynamically adjustable by SUBP ADJUST controls 1102, which are responsive to controls that originate from the risk analyzer 1300 (FIG. 13). Accordingly, SUBP ADJUST 1102 advantageously responds to discrete realtime data, such as test results, and non-realtime data, such as known disease conditions, family history, genetics and the like. Accordingly, the relative weights 850 for one or more sub-parameter risks 840 are also responsive to SUBP ADJUST controls 722.

Figure 12:
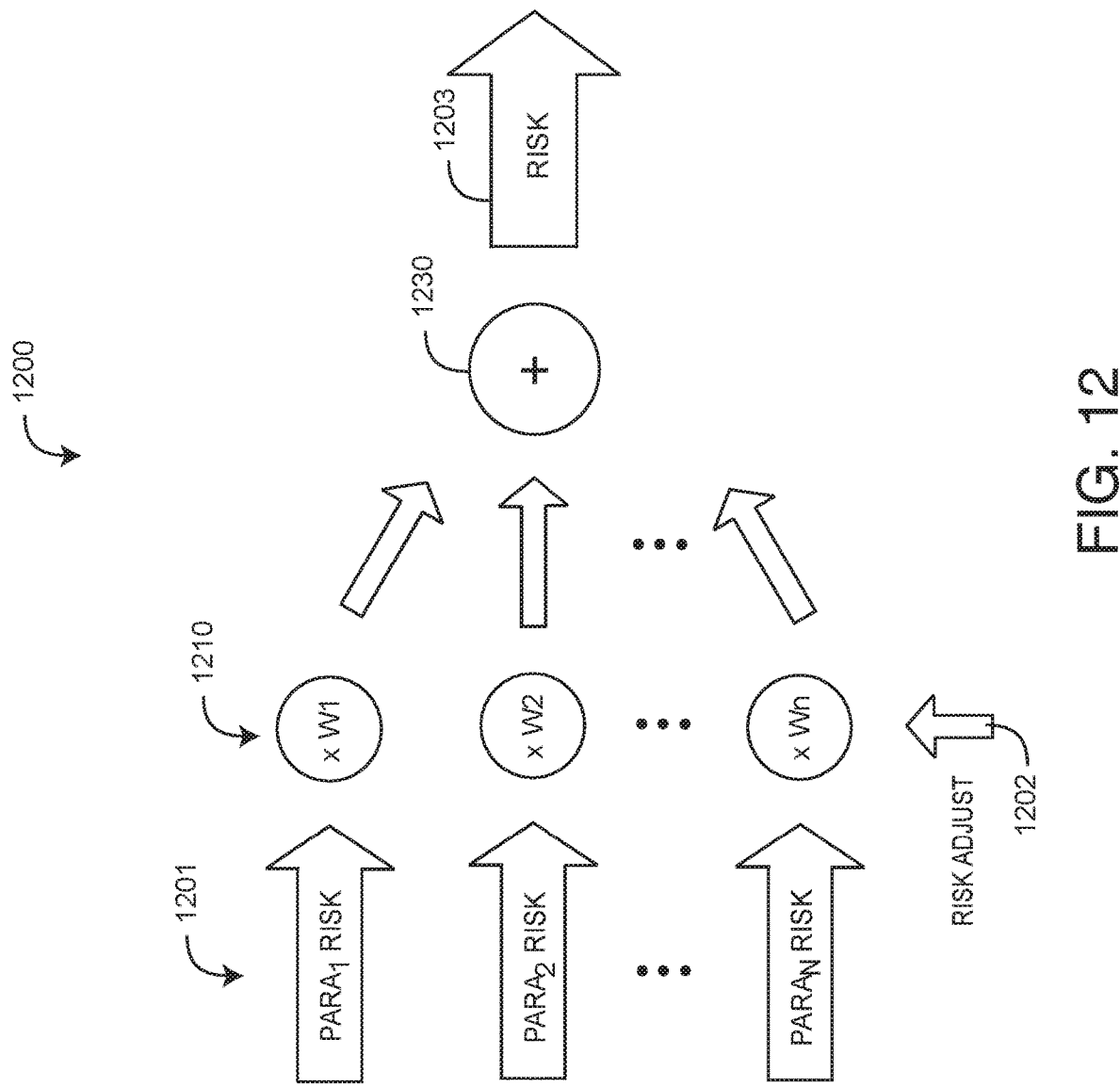
FIG. 12 is a flow diagram of a parameter risk calculator embodiment.

FIG. 12 illustrates a total risk calculation 1200 having parameter risk 1201 inputs and generating a risk 1203 output. In an embodiment, the parameter risks 1201 are assigned parameter risk weights 1210 so that the risk 1201 ranges between 0 to 1. Some parameter risks 1201 are assigned a higher weight to reflect a higher relative contribution of those parameters risks 1201 to the (total) risk 1203 output.

As shown in FIG. 12, the parameter weights 1210 are advantageously adjustable by RISK ADJUST 1202, which originates from the risk calculation controller 1030 (FIG. 10) and is responsive to controls 1303 (FIG. 13) from the risk analyzer 1300 (FIG. 13). For example, a user can advantageously determine the impact an individual parameter has on risk 1203 over any given time span by utilizing the risk analyzer 1300 (FIG. 13) to assign a zero weight 1210 to that parameter and adjusting other weights 1210 accordingly via controls 1303 (FIG. 13) and RISK ADJUST 1202. As another example, weights 1210 can be adjusted to reflect newly received test data or historical or background information, which indicate that relative parameter risks have changed. As a further example, weights 1210 can be adjusted as described above to reflect a recorded parameter that is active only for a specified time period. As yet another example, some weights 1210 can be zeroed and other weights 1201 adjusted accordingly if one or more parameters are disconnected or otherwise become inactive.

FIG. 13 illustrates a risk analyzer 1300 that functions in conjunction with a risk processor 1000 (FIG. 10) to re-characterize a medical risk calculation. Risk re-characterization may involve incorporating new or previously unused data into a risk calculation. Such data includes realtime discrete data, such as a lab test that generates a later result; non-realtime discrete data, such as a datum of medical history; and a time segment of previously recorded parameter data, to name a few. Risk re-characterization may also involve recalculating risk excluding one or more previously included parameters so as to allow a user to determine the impact on risk of those parameters.

As shown in FIG. 13, the risk analyzer 1300 has a record requester 1310 and a risk processor controller 1320. The record requester 1310 is responsive to a data ID 1301 input so as to generate a record ID 1302 output to the data storage 930 (FIG. 9). The data ID 1301 originates from user I/O 920 (FIG. 9) according to a user selection of previously excluded data, as described with respect to FIG. 9, below. In particular, the record ID 1302 specifies one or more data records 932 (FIG. 9) to retrieve from the data storage 930 (FIG. 9) for the risk processor 1000 (FIG. 9). These records may include parameters and data previously used to calculate risk along with records of heretofore unused parameters and data that the user 50 (FIG. 9) has currently selected, collectively "active" data.

Also shown in FIG. 13, the record requester 1310 communicates this "active" data 1312 to the risk processor controller 1320, which generates controls 1303 to the risk processor 1000 (FIG. 9). These controls 1303 include PARA 1001, RT 1003 and NT 1005 outputs for signaling the risk processor 1000 (FIG. 9) which parameters and discrete data to include in the current calculation of risk. In particular, PARA 1001 specifies which input parameters 912 (FIG. 9) are active. RT 1003 specifies discrete real-time data and NT 1005 specifies non-real-time data to be used in the risk calculations. The risk calculation controller 1030 (FIG. 10) responds to PARA 1001 to generate risk adjust 1034 (FIG. 10), which causes the risk calculation 1200 (FIG. 12) to ignore inactive parameters, as described above. The risk calculation controller 1030 (FIG. 10) also responds to RT 1003 to generate sub-parameter adjust 1032 (FIG. 10), which causes the parameter risk calculator 1000 (FIG. 10) to modify sub-parameter risks 1140 (FIG. 11) to account for real-time discrete data. The risk calculation controller 1030 (FIG. 10) further responds to NRT 1005 to generate sub-parameter adjust 1032 (FIG. 10), which causes the parameter risk calculator 1010 (FIG. 10) to factor in particular subject data, as described above.

FIG. 14 illustrates a user input/output (I/O) 1400 that provides user display and control for risk characterization and recharacterization of input parameters and data. The user I/O 1400 has a marker generator 1410 and a user interface 1420. The marker generator 1410 advantageously flags test and result epochs on a user display, as illustrated and described with respect to FIGS. 8A-D, below. In particular, the marker generator 1410 has a parameter record input 1401 from the data store and generates flags 1403 to a display 940 (FIG. 9). The flags 1403 are advantageously used to identify the occurrence of test data and later results relative to a risk record. A user interface 1420 is responsive to user selections 1402 from a user input to select 1402 one or more of these epochs, which may cause the marker generator 1410 to highlight a particular flag or otherwise indicate its selection the display. Further, the user selection 1402 generates a data ID 1404 to the risk analyzer 1300 (FIG. 13), which generates a record ID 1302 (FIG. 13) and controls 1303 (FIG. 13) so as to access the selected data from the data storage and process the data in the risk processor 1000 (FIG. 10) accordingly.

A medical characterization system has been disclosed in detail in connection with various embodiments. These embodiments are disclosed by way of examples only and are not to limit the scope of the claims that follow. One of ordinary skill in the art will appreciate many variations and modifications.

What is claimed is:

1. A method of determining a health index that can be used by a care provider for treating a patient, the method comprising:
   receiving optical data from an optical sensor;
   determining a plurality of parameters based on the received optical data, wherein at least one of the plurality of parameters comprise oxygen saturation;
   extracting a plurality of subparameters corresponding to the oxygen saturation, wherein the subparameters comprise saturation baseline, saturation instability, and saturation average slope;
   applying a respective risk function to each of the plurality of subparameters;
   calculating a plurality of subparameter risk values based on the application of respective risk functions;
   calculating an oxygen saturation risk based on an application of a plurality of weights to the calculated plurality of subparameter risk values;
   generating a health index based on the calculated oxygen saturation risk and risks associated with rest of the plurality of parameters;
   displaying the health index as a trend line over a time period on a display;
   generating an indication on the trend line at a second time later than a first time that a result of a test that was performed at the first time is available;
   and
   responsive to a selection by the care provider of the indication, altering the health index trend line between the first time and the second time based on the result, the first time, and the second time.

2. The method of claim 1, further comprising allowing a user to dynamically include or exclude the plurality of parameters from calculation of the health index and updating the health index based on the user selection.

3. The method of claim 1, further comprising modifying the health index based on non-real-time data.

4. The method of claim 1, wherein the plurality of weights are automatically selected based on active data.

5. The method of claim 1, wherein the plurality of weights are automatically selected based on user defined criteria.

6. The method of claim 1, wherein the displaying further comprises displaying a historical trend of the health index.

7. The method of claim 1, wherein the displaying further comprises displaying a plurality of markers.

8. The method of claim 1, wherein the plurality of parameters comprise real-time and non-real-time parameters.

9. A system for determining a health index that can be used by a care provider for treating a patient, the system comprising one or more hardware processors configured to:
   receive optical data from an optical sensor;
   determine a plurality of parameters based on the received optical data, wherein at least one of the plurality of parameters comprise oxygen saturation;
   extract a plurality of subparameters corresponding to the oxygen saturation;
   apply a respective risk function to each of the plurality of subparameters;
   calculate a plurality of subparameter risk values based on the application of respective risk functions;
   calculate an oxygen saturation risk based on an application of a plurality of weights to the calculated plurality of subparameter risk values;
   generate a health index based on the calculated oxygen saturation risk and risks associated with rest of the plurality of parameters; and
   display the health index as a trend line over a time period, wherein the health index is configured to provide a caregiver information for treating the patient;
   generate an indication on the trend line at a second time later than a first time that a result of a test that was performed at the first time is available; and
   responsive to a selection by the care provider of the indication, alter the health index trend line over between the first time and the second time based on the result, the first time, and the second time.

10. The system of claim 9, wherein the one or more hardware processors are further configured to allow a user to dynamically include or exclude the plurality of parameters from calculation of the health index and update the health index based on the user selection.

11. The system of claim 9, wherein the one or more hardware processors are further configured to modify the health index based on non-real-time data.

12. The system of claim 9, wherein the plurality of weights are automatically selected based on active data.

13. The system of claim 9, wherein the plurality of weights are automatically selected based on user defined criteria.

14. The system of claim 9, wherein the one or more hardware processors are further configured to display a historical trend of the health index.

15. The system of claim 9, wherein the one or more hardware processors are further configured to display a plurality of markers.

16. The system of claim 9, wherein the subparameters comprise saturation baseline, saturation instability, and saturation average slope.

* * * * *